United States Patent
Thalhammer et al.

(10) Patent No.: US 8,573,073 B2
(45) Date of Patent: Nov. 5, 2013

(54) METHOD AND DEVICE FOR TRANSFERRING A MICROSCOPIC, ISOLATED SAMPLE

(75) Inventors: Stefan Thalhammer, Munich (DE); Norbert Hohn, Darmstadt (DE); Albert Zink, Munich (DE); Wolfgang Heckl, Munich (DE)

(73) Assignee: Helmholtz Zentrum Muenchen Deutsches Forschungszentrum fur Gesundheit und Umwelt GmbH, Neuherberg (DE)

( * ) Notice: Subject to any disclaimer, the term of this patent is extended or adjusted under 35 U.S.C. 154(b) by 375 days.

(21) Appl. No.: 12/842,802

(22) Filed: Jul. 23, 2010

(65) Prior Publication Data

US 2011/0061476 A1    Mar. 17, 2011

Related U.S. Application Data

(63) Continuation of application No. PCT/EP2008/067208, filed on Dec. 10, 2008.

(30) Foreign Application Priority Data

Jan. 25, 2008 (EP) .................. 08150662

(51) Int. Cl.
*B01L 3/02* (2006.01)

(52) U.S. Cl.
USPC .................. 73/864.11; 73/864.21

(58) Field of Classification Search
USPC ............. 73/864.31, 864.01
See application file for complete search history.

(56) References Cited

U.S. PATENT DOCUMENTS

| | | | |
|---|---|---|---|
| 6,998,047 B1 * | 2/2006 | Kopaciewicz et al. | ... 210/321.75 |
| 7,521,020 B2 * | 4/2009 | Gratzl et al. | ............. 422/509 |
| 7,632,462 B2 * | 12/2009 | Holtlund et al. | ............. 422/65 |
| 2005/0258097 A1 * | 11/2005 | Gjerde et al. | ............. 210/635 |

FOREIGN PATENT DOCUMENTS

| | | |
|---|---|---|
| EP | 0539888 A1 | 5/1993 |
| JP | 4-023750 | 1/1992 |

(Continued)

OTHER PUBLICATIONS

Schindler M., "A Cut Above the Rest," *The Biochemist*, Oct. 2002, pp. 25-28 XP002485626.

(Continued)

*Primary Examiner* — Hezron E Williams
*Assistant Examiner* — Nashmiya Fayyaz
(74) *Attorney, Agent, or Firm* — Jenkins, Wilson, Taylor & Hunt, P.A.

(57) ABSTRACT

A method and a device for transferring a microscopic, isolated sample, particularly a membrane-supported micro-dissected specimen, from an object table to an analysis arrangement, with a suction apparatus comprising a nano-suction means with a suction tube and a terminal membrane and a vacuum/overpressure unit which can be coupled to the nano-suction means for sucking or blowing the sample onto or from the terminal membrane; and a carrier apparatus for carrying the nano-suction means, which can be moved by means of an associated positioning unit for positioning the nano-suction means exactly in a sample removal position for sucking the sample onto the terminal membrane and in a sample release position for blowing the sample from the terminal membrane. A micro-dissection system, comprising such a device and a method for the production of a nano-suction means that is used in such a device.

24 Claims, 3 Drawing Sheets

(56) References Cited

FOREIGN PATENT DOCUMENTS

| | | |
|---|---|---|
| JP | 10-273224 | 10/1998 |
| JP | 11-118810 | 4/1999 |
| JP | 2000-515015 | 11/2000 |
| JP | 2005-233960 | 9/2005 |
| WO | WO 98/03628 | 1/1998 |
| WO | WO 98/44972 | 10/1998 |
| WO | WO 2007/054161 | 5/2007 |

OTHER PUBLICATIONS

Stark, Robert W. et al., "Combined Nanomanipulation by Atomic Force Microscopy and UV-laser Ablation for Chromosomal Dissection," *European Biophysics Journal*, Mar. 2003, pp. 33-39 XP 002485627.

International Search Report for PCT/EP2008/067208 dated Mar. 30, 2009.

Japanese Office Action for Application No. 2010-543404 dated Nov. 12, 2012.

* cited by examiner

METHOD AND DEVICE FOR TRANSFERRING A MICROSCOPIC, ISOLATED SAMPLE

CROSS-REFERENCE TO RELATED APPLICATIONS

This application is a continuation of PCT/EP2008/067208 filed Dec. 10, 2008 and claims the benefit of European Patent Application No. 08 150 662.8 filed Jan. 25, 2008, the entire disclosure of which is herein incorporated by reference.

FIELD OF THE INVENTION

The present invention relates to a method and a device for transferring a microscopic, isolated sample, particularly a membrane-supported micro-dissected specimen, from an object table to an analysis arrangement, a micro-dissection system comprising such a device and a method for producing a nano-suction means for such a device.

Although it can be used on any microscopic, isolated samples, the present invention and the underlying problems are explained in greater detail with reference to membrane-supported micro-dissected specimens, and particularly micro-dissected specimens isolated by means of laser-supported micro-dissection.

Laser-supported micro-dissection makes it possible to deliberately isolate the smallest areas from a tissue section right down to individual cells. Contact-free laser manipulation can also guarantee micro-dissection of individual cell compartments, e.g. chromosomes and fragments of chromosomes. It is possible to develop region-specific chromosomal samples for molecular cytogenetics by a combination of PCR, cloning techniques and laser micro-dissection. However, in these laser micro-dissection methods, the fragments are collected with a glass needle, which has been drawn out to be as fine as possible, similar to glass needle micro-dissection. A development in laser micro-dissection has led to the introduction of laser capture micro-dissection. In this method a synthetic membrane is applied to the tissue to be examined. The cells to be isolated are removed from the tissue by melting the film locally by applying heat. This method is particularly suitable for isolating cell groups down to a size of approx. 30 µm.

The principle of laser pressure isolation is a different method for isolating individual cells and cell groups. In this technique a pulsed UV laser with power peaks of a few watts is directed onto the area of tissue to be isolated from below. Unlike in laser capture micro-dissection, the tissue is placed on an ultrathin support membrane which is between approx. 1 and 6 µm thick. Cells or cell groups can be deliberately isolated using the UV laser and in a further stage these are isolated upwards onto a collection device with the aid of light pressure, to make them accessible for other biochemical methods. Isolation of chromosomes to develop chromosome-specific paint samples has been introduced using this method.

However, in the above-mentioned methods which are already known in the art, the fact that it is not possible to guarantee transfer of the isolated sample has proved to be a disadvantage and these methods may cause damage or contamination of the sample to be transferred. In addition, in the above-mentioned methods, optical monitoring of the entire transfer process is only possible with great difficulty, if at all. Furthermore, defined picking-up and setting-down of the sample is not guaranteed due to the means of transfer used.

For example, damage to tissue particles, cells and cell components, proteins and kinetic material may arise in the catapulting process in the above-mentioned methods. In glass needle micro-dissection, the sample is disadvantageously scraped off, resulting in damage to the sample due to the nature of this method.

SUMMARY OF THE INVENTION

As a result, in the light of the above-mentioned, known methods, the object of the present invention is to eliminate the above-mentioned disadvantages and in particular to improve a device and a method for transferring a microscopic, isolated sample in such a way as to guarantee that the corresponding sample is transferred more carefully and in a more defined manner from an object table to an analysis arrangement.

This object is achieved according to the invention by a device with the features of claim 1, a micro-dissection system with the features of claim 19, a method with the features of claim 22 and a method for producing a nano-suction means with the features of claim 26.

The concept underlying the present invention entails using a suction apparatus to transfer a microscopic, isolated sample, this suction apparatus having a nano-suction means with a suction tube and a terminal membrane and a vacuum/over-pressure unit which can be coupled to the nano-suction means for sucking or blowing the sample onto or from the terminal membrane; a carrier apparatus for carrying the nano-suction means is provided, this being adjustable by means of an associated positioning unit for positioning the nano-suction means exactly in a sample removal position for sucking the sample onto the terminal membrane and in a sample release position for blowing the sample from the terminal membrane.

The present invention thus has the advantage over the known methods of preventing damage to the isolated sample due to the careful suction or blowing of the sample onto or from the terminal membrane and guaranteeing a simple means of exact, defined and controllable transfer of the sample by the carrier apparatus in conjunction with the associated positioning unit.

Preferential embodiments and improvements of the device and method for transferring a microscopic, isolated sample, the micro-dissection system comprising such a device and the method for producing a nano-suction means, as used in such an invention, can be found in the sub-claims.

The extraction point is preferably adjusted horizontally either under observation of the microscope unit by motor control via a joystick or automatically by digital position transfer. A distance meter or autofocus secured by mechanical means to the nano-suction means makes it possible to lower the nano-suction means accurately to within µm to a pre-defined suction level above the extraction point. The distance meter continuously measures the actual distance from the surface and compares this with a pre-defined set distance. When the nano-suction means reaches the pre-defined set distance as it is lowered, the convergence process stops and the suction process is activated. The vacuum sucks the sample onto the terminal membrane and keeps it there.

The nano-suction means is then positioned in the release position by means of the positioning unit. The vacuum should preferably remain throughout the entire positioning process. When the nano-suction means reaches its release position, it is lowered to a pre-defined set position by means of the distance meter in the same way as described above. An over-pressure is applied in this position to blow the extracted sample into the analysis area.

BRIEF DESCRIPTION OF THE DRAWINGS

The invention is explained below in greater detail with the aid of embodiments and with reference to the attached figures in the drawing. The figures show.

DESCRIPTION OF EXEMPLARY EMBODIMENTS

Figure 1:
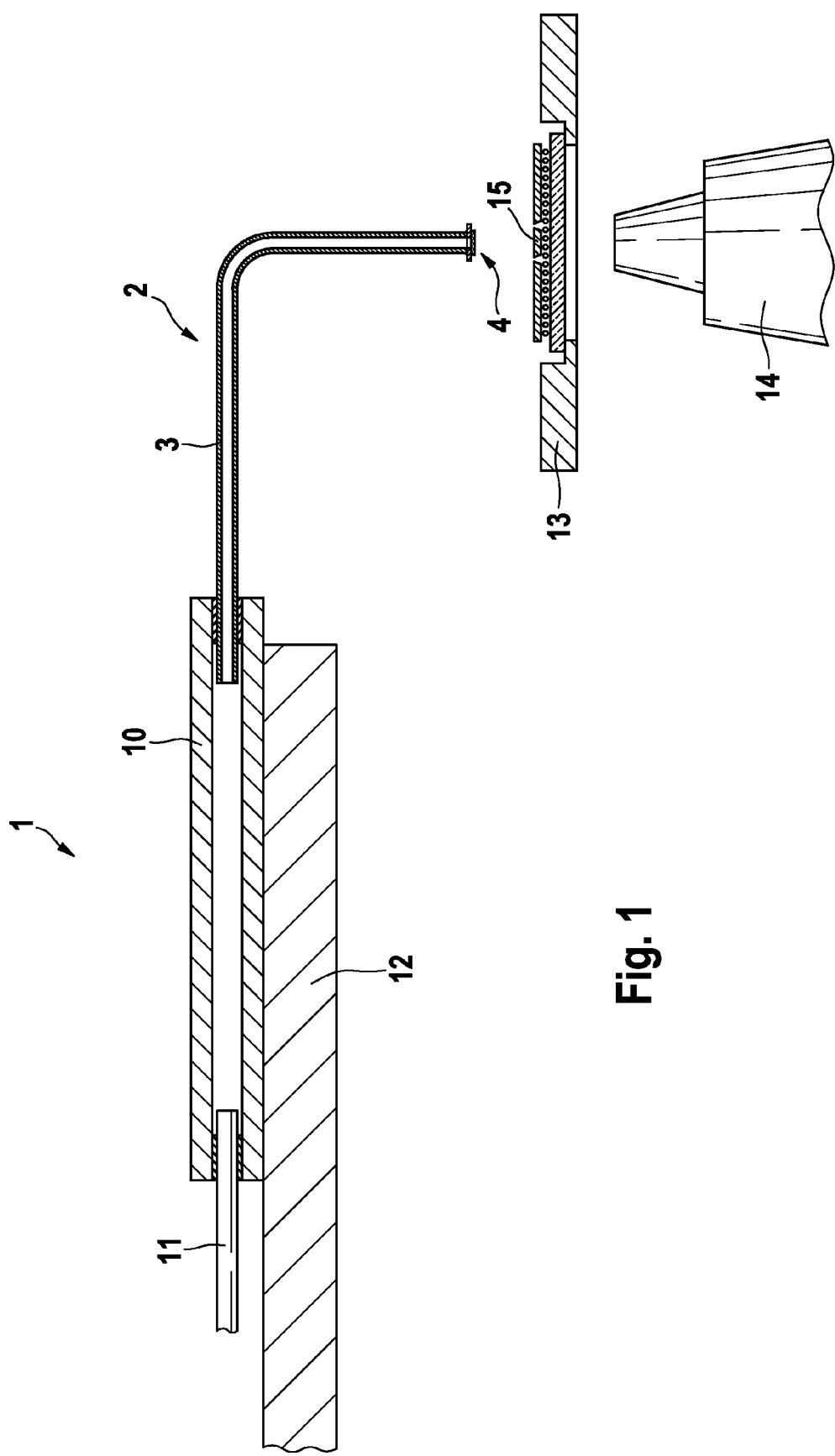
FIG. 1 a schematic partial view of a transfer device in accordance with a preferred embodiment of the present invention which is incorporated within a micro-dissection system.

In the figures, the same reference numerals refer to the same components or components with the same function, unless otherwise specified.

FIG. 1 shows a schematic partial view of a transfer device incorporated in a micro-dissection system in accordance with a preferred embodiment of the present invention for transferring isolated tissue sections or cells, referred to hereafter as sample 15, especially after laser micro-dissection. The transfer device is preferably designed to be autonomous and able to be incorporated in existing systems, for example fixed to an existing microscope unit 14 of the micro-dissection system.

In accordance with the present embodiment, the transfer device has a suction apparatus 1 which is used to suck the sample 15 from an object table 13 in the sample removal position shown in FIG. 1 or to blow the sample 15 in a sample release position which is not shown. The object table 13 may for example be designed both as a microscope platform of an associated microscope unit and as an independent microscope platform in which an object carrier can be clamped with a support membrane for example. It should be noted at this juncture that in laser micro-dissection the sample 15 is generally located on a support membrane and transported along with this membrane by the transfer device from the object table 13 to an analysis arrangement which is not illustrated.

The suction apparatus 1, as illustrated schematically in FIG. 1, has a nano-suction means 2 which may, for example, comprise a borosilicate glass tube 3 and a terminal membrane 4. In accordance with the present embodiment, the glass tube 3 is L-shaped, as shown in FIG. 1, with a long section and a short section. The long section provides an airtight connection with a coupling tube 10, as described in greater detail below.

The short section of the glass tube 3 has a terminal membrane 4 at its free front end. This top end of the nano-suction means 2 is illustrated in an enlarged cross-sectional view in FIG. 2. The glass tube 3 may, for example, have an external diameter of between approx. 1.7 mm and 2.0 mm, an internal diameter of between approx. 0.5 mm and 1.5 mm and an overall length, i.e. including the length of both sections, of approx. 50 mm to 70 mm.

Figure 2:
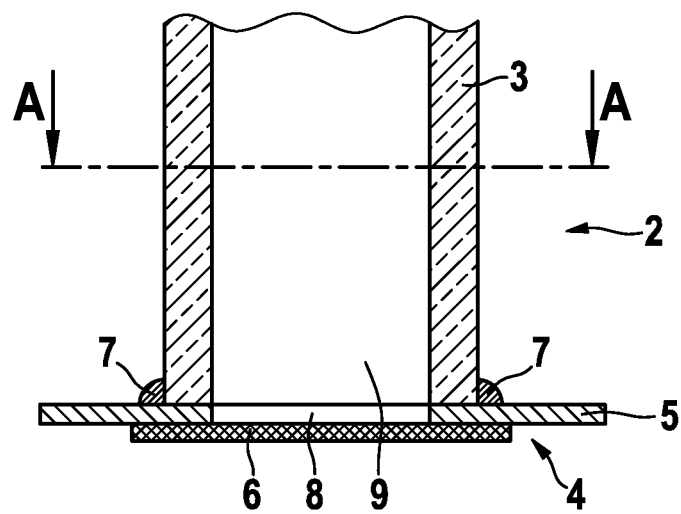
FIG. 2 an enlarged cross-sectional view of the top end of the nano-suction means in accordance with a preferred embodiment of the present invention.

The suction tube or glass tube 3 is also vapour-plated with an electroconductive coating, at least in some sections, and in particular in the end region of the top area shown in FIG. 2, with an electroconductive gold coating which may for example be approx. 60 nm thick.

Figure 3:
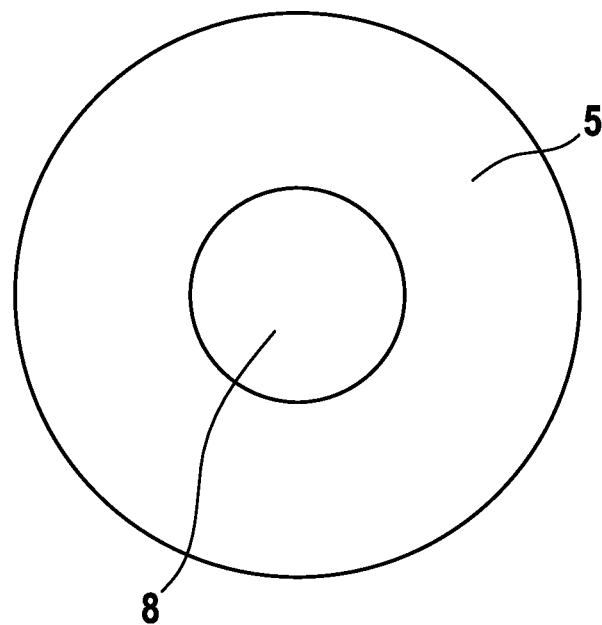
FIG. 3 a view from above of a support plate for the nano-suction means in accordance with a preferred embodiment of the present invention.

As is also shown in FIG. 2, the terminal membrane 4 comprises a support plate 5 and a terminal mesh 6. The support plate 5 is illustrated separately and in an enlarged view in FIG. 3, showing that the support plate 5 may, for example, be designed as a disc with a hole 8 in the centre. The support plate 5 is preferably made from an electroconductive material such as copper or something similar. With reference to FIG. 2, the support plate 5 is preferably fixed to the end of the top section of the nano-suction means 2 such that the hole 8 is flush with the opening 9 in the suction tube 3. However, it is also conceivable that another embodiment may be selected, although the entire suction power should advantageously be directed through the hole 8.

Figure 4:
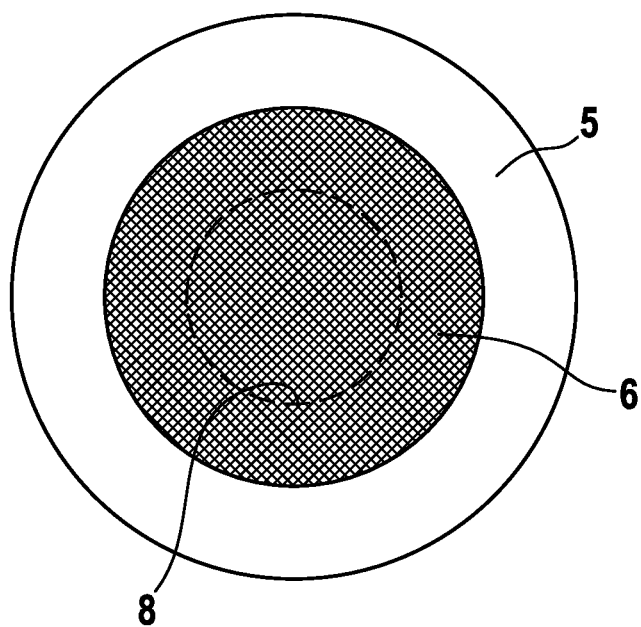
FIG. 4 a schematic view of a terminal membrane comprising a support plate and terminal mesh in accordance with a preferred embodiment of the present invention.

The terminal membrane 4 also has a terminal mesh 6 which is also made from an electroconductive material or a material with an electroconductive surface. FIG. 4 shows a view from beneath the terminal membrane 4 comprising a support plate 5 and terminal mesh 6. The terminal mesh 6 may, for example, be in the form of a round disc. The dimensions of the nano-suction means, i.e. both the suction tube 3 and the support plate 5 and terminal mesh 6, may be varied as a function of the relevant application. In particular, the thickness of the mesh and the pore size of the terminal mesh 6 should be adjusted appropriately to the relevant sample 15 to be transferred. A mesh thickness of approx. 20 μm and pores with a diameter of between approx. 60 nm and 50 μm are conceivable, for example.

The terminal mesh 6 is preferably placed on the support plate 5 such that the mesh fully covers the hole 8 in the support plate 5 and thus the opening 9 of the suction tube 3, as is also shown in FIG. 2. The whole structure is designed such that the suction air is passed directly through the mesh 6 and not to the environment at any places which are not sealed.

Figure 5:
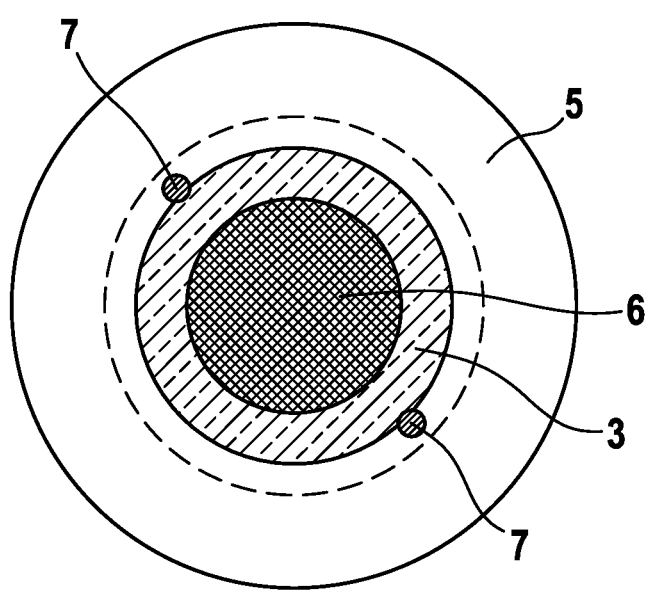
FIG. 5 a cross-sectional view along line A-A in FIG. 2.

FIG. 5 shows a cross-sectional view along line A-A in FIG. 2. Any electrostatic charge on the nano-suction means 2 should be prevented to protect the sample 15. As shown in FIG. 5 together with FIG. 2, electrical contact points 7 are provided, in the form of conductive silver paint or something similar, for example, to create an electrical connection between the support plate 5 and the electroconductive coating on the suction tube 3. This is intended to advantageously divert electrostatic charges which may, for example, be caused by certain samples or the terminal membrane 4 material, via the suction tube 3 or one of the earth wires associated with the suction tube 3.

We shall once again refer to FIG. 1 to describe further features of the transfer device, although the transfer device is only shown schematically and in part for the sake of clarity.

For example, the suction apparatus 1, as already described above, has a coupling tube 10, into which the free end of the long section of the suction tube 3 can be inserted and fixed in position in an airtight fashion and such that it can easily be replaced. The coupling tube preferably has a clip or turn fastening by which the nano-suction means 2 can be connected and disconnected to/from the suction apparatus 1 for replacement purposes. For example, a turn fastening with a corresponding rubber seal is provided which either holds the associated end of the suction tube 3 in the coupling tube 10 in an airtight fashion or releases this end from the coupling tube 10 to remove the suction tube 3 by turning this fastening accordingly.

At the opposite end of the coupling tube 10, there is a connection 11 for connecting an associated vacuum/overpressure unit which is not illustrated. It is also conceivable that a corresponding adaptable clip or turn fastening could be provided in this case. It is also conceivable that a Teflon hose of precisely the right size could be put over the corresponding end of the coupling tube 10 and further sealed with silicone.

The vacuum/overpressure unit may, for example, be designed as a pneumatic pico-pump which supplies the required vacuum for suction of the sample 15 onto the terminal mesh 6 or the required overpressure to blow the sample 15 from the terminal mesh 6. For example, a sensitive PLI-100 pressure control unit is used which makes it possible to accurately set a low pressure of approximately 0 to 0.75 kPa, but also a high pressure, e.g. 413 kPa, for sucking or blowing the sample respectively. The suction power or the strength of the blowing pulse of the vacuum/overpressure unit is preferably predetermined and adjusted accordingly in line with the relevant application. It is also advantageous if the overpressure duration can be adjusted to several ms in order to release the collected sample safely into a provided drop of liquid on the analysis arrangement without dispersing this drop.

As shown in FIG. 1, the transfer device also comprises a carrier apparatus 12 to which at least the coupling tube 10 and thus the nano-suction means 2 of the suction device 1 are fixed. The carrier apparatus 12 is connected to an associated positioning unit which is not illustrated. Four degrees of freedom of the positioning unit are preferably provided in order to move the carrier apparatus 12, as already mentioned above, with three translational movements (directions x, y and z), and a rotational movement to swivel the carrier apparatus 12 in a horizontal plane. For example, a micrometer stepper motor is used which can position the carrier apparatus 12 and thus the nano-suction means 2 accurately within the μm range. If the transfer device is fitted to an associated microscope unit 14, this means that only the object table can be moved accordingly, guaranteeing accurate positioning of the nano-suction means 2 above the lens system or laser system of the microscope unit 14 when the carrier apparatus 12 is swivelled, as the carrier apparatus 12 is moved within the microscope unit 14 reference system due to it being fixed in position. This guarantees maximum accuracy and rapid extraction of the relevant samples, even very small samples. The entire adjustment movement is executed by corresponding software and a control unit.

In addition, the transfer device may, if required, have additional components which are not illustrated in the figures for the sake of clarity. For example, a display unit is provided for optical monitoring and display of the transfer process.

The display unit may, for example, consist of a CCD camera with a flexible API interface. A distance meter is also provided, for example an appropriate laser sensor, which measures online the distance between the terminal membrane 4 and the sample to be removed 15 or the distance from an analysis arrangement on which the extracted sample 15 is to be placed. For example, an LTA-02 laser sensor autofocus unit may be used as a laser sensor for automatic distance control, which automatically adjusts a set distance of say 100 μm between the relevant surfaces. This laser sensor may also advantageously be designed to be adjusted mechanically by means of the above-mentioned micrometer stepper motor.

The list of above-mentioned components should not be regarded as being finite and experts will be well aware of additional components which they can incorporate in the transfer device in the relevant applications. Furthermore, experts will also be well aware that the above-mentioned components can be connected to the shared control unit and corresponding software such as to ensure user-friendly transfer of the relevant sample 15 from the object table 13 to an associated analysis arrangement, e.g. by means of an associated joystick and for display on a corresponding monitor.

As already pointed out above, it may be preferable to incorporate the described transfer device in a micro-dissection system. In this case, it is advantageous to fix the transfer device, which is designed as an autonomous system, to an existing microscope unit 14, such as to provide a common reference system. This makes it much easier to position the nano-suction means 2 above the lens and/or laser system of the microscope unit 14, as precise positioning is achieved merely by a rotational swivelling movement of the carrier apparatus 12, for example. In this case, it is merely necessary to lower the nano-suction means 2 accordingly by means of the associated distance meter and to move the object table 13 and thus the sample 15 horizontally to ensure fine adjustment.

It is advantageous if the transfer device basically operates independently and thus autonomously from the subsequent analysis stages and can thus be incorporated in existing systems in a modular fashion. This creates considerable potential with respect to scientific usage, but also for further possible industrial marketing of this technology.

A preferred embodiment of a method for producing a nano-suction means 2 will be explained in further detail below, where this nano-suction means plays a crucial role in ensuring exact transfer of a sample 15 without leading to damage or contamination of this sample.

A borosilicate glass tube 3 with an external diameter of between approximately 1.7 mm and 2.0 mm and an internal diameter of between approximately 0.5 mm and 1.5 mm is, for example, formed in an L-shape by means of a corresponding device such that the glass tube 3 preferably has one longer section and one shorter section, as shown in FIG. 1. The glass tube 3 bent in this way is then vapour-plated with a gold coating which is 60 nm thick, for example, in a pre-defined area, preferably the top part of the shorter section. This gold coating means that the corresponding surface of the glass tube 3 is electroconductive, but does not alter the transparent properties of the glass tube 3.

The edge of the shorter section of the glass tube 3 is then preferably coated with a UV-hardening adhesive. The glass tube 3 is then placed in the exact centre above the support plate 5 and lowered micromechanically until the adhesive-coated edge of the glass tube 3 comes into contact with the support plate 5. The UV adhesive is than hardened with a UV lamp, resulting in a permanent connection between the support plate 5 and the glass tube 3.

A 0.5 mm wide strip of adhesive, for example, preferably of a UV-hardening adhesive, is When applied on the free underside of the support plate 5 around the hole 8 in the support plate 5. The glass tube 3, together with the previously attached support plate 5, is then lowered micromechanically onto the terminal mesh 6, and the applied adhesive is once again hardened by means of a UV lamp after joining the support plate 5 and the terminal mesh 6.

Finally, an electroconductive connection between the support plate 5 and the conductive surface or the vapour-plated electroconductive coating on the glass tube 3 is established, which can be achieved, for example, by applying two drops of conductive silver paint to opposite sections.

The transfer device preferably has a set of different nano-suction means 2, the individual nano-suction means 2 having different terminal membranes 4 or terminal mesh 6. In this case, the dimensions, material, pore size and pore configuration of the terminal mesh 6 may vary, as may its other properties, with the result that an appropriate nano-suction means 2 is selected as a function of the sample 15 to be transferred in each case and connected manually, in an airtight fashion, to the coupling tube 10 for incorporation in the suction device and thus in the transfer device. As a result, the user can simply and manually select the appropriate nano-suction means 2 from the existing set and fit it in the transfer device as a function of the sample 15 to be transferred in each case. This also has the advantage that any damaged nano-suction means can be replaced very simply.

A method for transferring a sample 15 from an object table 13 to an analysis arrangement in accordance with a preferred embodiment of the present invention will again be described in greater detail below with particular reference to FIG. 1. In this case it is assumed by way of example that the transfer device is fixed to a microscope unit 14 and a sample is isolated by means of laser micro-dissection using an associated micro-dissection system.

A sample specimen is first placed on an associated glass plate of the object table 13 and positioned by means of a lens system or laser system in the microscope unit 14. Part of the sample specimen is then cut out by means of laser micro-dissection, for example, to isolate the sample 15 to be transferred. The nano-suction means 2 is then swivelled in a horizontal plane above the sample 15 or the lens system of the microscope unit 14 by moving the carrier apparatus 12 via the positioning unit and, if necessary, its height is adjusted automatically or manually by means of the associated distance meter.

The isolated sample 15 is then sucked from the object table 13 onto the terminal mesh 6 of the nano-suction means 2 by setting a low pressure in the vacuum/overpressure unit, for example a pressure of less than 0.75 kPa. The carrier apparatus 12 is then moved precisely from the object table 13 to the associated analysis arrangement by means of the existing positioning device whilst maintaining the suction pressure.

A small drop of liquid may for example, be provided on the analysis arrangement for analysing the transferred sample 15 in order to catch the sample 15. The carrier apparatus 12 is then lowered once again to a pre-defined distance, e.g. 100 µm above the surface of the drop, and the sample 15 is then carefully and precisely blown out onto the drop by changing the vacuum/overpressure unit to a short pulse of higher pressure, e.g. a pressure of 413 kPa for 2 ms.

This makes it possible to transfer the isolated sample 15 precisely and carefully into a reaction vessel for further analysis.

As already described above, the nano-suction means 2 is preferably moved to a distance approx. 100 µm from the sample surface or the surface of the drop during the suction or blowing process. This may, for example, be guaranteed by incorporating an LTA-02 laser sensor. As the nano-suction means 2 approaches the corresponding surface, the laser sensor constantly measures the distance to the surface. This difference between the set and actual distances is then transmitted to the control unit and reflected back in terms of the movement of the nano-suction means 2 or the carrier apparatus 12 in the focus direction. If the difference is greater than 0, the movement continues. If the set distance corresponds to the actual distance, the nano-suction means 2 focus movement stops and the suction or blowing process can commence.

Although the present invention has been described in this case by means of preferred embodiments, it is not limited to these embodiments, but may be modified in multiple ways. In particular, the dimensions, materials and properties of components given above by way of example may be modified in accordance with the respective application. The key factor is merely that the isolated sample is transferred by means of a corresponding suction apparatus which can be positioned precisely in specific positions by means of a carrier apparatus, and particularly in the horizontal direction of movement.

The present invention thus has the advantage that samples can be transferred in a careful and exactly reproducible manner which can be monitored by visual means, and the corresponding system is designed to be autonomous and can thus be incorporated in existing systems.

In the following, preferred embodiments of the device, the micro-dissection system, the method for transferring a microscopic isolated sample and the method for producing a nano-suction means are explained.

Embodiment 1: A device for transferring a microscopic, isolated sample, particularly a membrane-supported micro-dissected specimen, from an object table to an analysis arrangement, with: a suction apparatus which has a nano-suction means with a suction tube and a terminal membrane and a vacuum/overpressure unit which can be coupled to the nano-suction means for sucking or blowing the sample onto or from the terminal membrane respectively; and a carrier apparatus for carrying the nano-suction means, which can be moved by means of an associated positioning unit for positioning the nano-suction means exactly in a sample removal position for sucking the sample onto the terminal membrane and in a sample release position for blowing the sample from the terminal membrane.

Embodiment 2: The device according to embodiment 1, characterised in that the nano-suction means can be coupled in an airtight manner to the vacuum/overpressure unit by means of a coupling tube.

Embodiment 3: The device according to embodiment 2, characterised in that the coupling tube has connection devices, plug-in or clip connections for example, for manual connection of the vacuum/overpressure unit and/or a selected nano-suction means in an airtight fashion on a modular basis in such a way that different nano-suction means at least can easily be coupled manually, in an airtight fashion, to the vacuum/overpressure unit via the coupling tube.

Embodiment 4: The device according to at least one of the preceding embodiments, characterised in that the suction tube of the nano-suction means is designed as a glass tube, such as a borosilicate glass tube, for example.

Embodiment 5: The device according to at least one of the preceding embodiments, characterised in that the suction tube is approximately L-shaped and has an end which connects to the coupling tube and an end which connects to the terminal membrane.

Embodiment 6: The device according to at least one of the preceding embodiments, characterised in that the suction tube has an external diameter of between approx. 1.7 mm and 2.0 mm, an internal diameter of between approx. 0.5 mm and 1.5 mm and an overall length of approx. 50 mm to 70 mm.

Embodiment 7: The device according to at least one of the preceding embodiments, characterised in that the suction tube is coated with an electroconductive coating, at least in some sections, and in particular in the region of the end which is connected to the terminal membrane, for example with a gold coating which is approx. 60 nm thick.

Embodiment 8: The device according to at least one of the preceding embodiments, characterised in that the terminal membrane has a disc-shaped support plate, preferably with a hole in the centre and a terminal mesh, one side of the support plate being secured to the side of the terminal membrane connected to the suction tube in such a way that the hole in the support plate is approximately flush with the opening in the suction tube, and the terminal mesh being secured on the other free side of the support plate in such a way that the terminal mesh overlaps the opening in the suction tube and the hole in the support plate.

Embodiment 9: The device according to embodiment 8, characterised in that the support plate is made from an electroconductive material such as copper or something similar.

Embodiment 10: The device according to embodiment 8 or 9, characterised in that there is an electroconductive connection between the support plate and the electroconductive coating on the suction tube for earthing purposes, by using conductive silver paint or something similar, for example.

Embodiment 11: The device according to at least one of embodiments 8 to 10, characterised in that the terminal mesh is made from a material with an electroconductive surface.

Embodiment 12: The device according to at least one of embodiments 8 to 11, characterised in that the terminal mesh has a mesh thickness and a pore size which are adapted to the dimensions and nature of the sample to be transferred, for example a mesh thickness of approx. 20 μm and pores with a diameter of between approx. 600 nm and 5 μm.

Embodiment 13: The device according to at least one of embodiments 8 to 12, characterised in that the terminal mesh is designed to be biologically inert, antistatic and/or UVC-resistant.

Embodiment 14: The device according to at least one of the preceding embodiments, characterised in that the positioning unit is designed for a rotational movement and/or a translational movement of the carrier apparatus, for example by using a micrometer stepper motor.

Embodiment 15: The device according to at least one of the preceding embodiments, characterised in that the device also has a distance meter, for example a laser sensor or similar, for measuring the distance between the terminal membrane and the sample to be transferred or the relevant surfaces.

Embodiment 16: The device according to at least one of the preceding embodiments, characterised in that the device has a display unit for visual display and monitoring of the transfer process.

Embodiment 17: The device according to at least one of the preceding embodiments, characterised in that the device has a control unit together with appropriate software which is connected to the carrier apparatus, the positioning unit, the vacuum/overpressure unit, the distance meter and/or the display unit for data exchange, control and adjustment purposes, etc.

Embodiment 18: The device according to at least one of the preceding embodiments, characterised in that the device is designed to be autonomous and can be integrated in a modular fashion in existing systems, for example a micro-dissection system.

Embodiment 19: A micro-dissection system which includes a device according to at least one of the preceding claims.

Embodiment 20: The micro-dissection system according to embodiment 19, characterised in that the micro-dissection system has a microscope unit to which the device can be secured.

Embodiment 21: The micro-dissection system according to embodiment 20, characterised in that the device can be secured to the microscope unit in such a way that the carrier apparatus can be moved in a defined manner with respect to the microscope unit reference system.

Embodiment 22: A method for transferring a microscopic, isolated sample, particularly a membrane-supported micro-dissected specimen, from an object table to an analysis arrangement, with the following method steps: exact positioning of a nano-suction means, which is designed with a suction tube and a terminal membrane and secured to a carrier apparatus in a sample removal position by moving the carrier apparatus by means of an associated positioning unit; suction of the sample onto the terminal membrane. by means of a vacuum/overpressure unit coupled to the nano-suction means; movement of the carrier apparatus for exact positioning of the nano-suction means in a sample removal position by means of the associated positioning unit; and blowing the sample from the terminal membrane. by means of the vacuum/overpressure unit.

Embodiment 23: The method according to embodiment 22, characterised in that the distance between the terminal membrane and the sample to be transferred or the relevant surfaces is measured continuously by means of a distance meter, for example a laser sensor, and is compared with a set value, the height position of the carrier apparatus. being adjusted by means of a control unit until the actual distance value corresponds to the set distance value.

Embodiment 24: The method according to embodiment 22 or 23, characterised in that an appropriate vacuum is maintained throughout the entire transfer process by the vacuum/overpressure unit.

Embodiment 25: The method according to at least one of embodiments 22 to 24, characterised in that a short pressure pulse is generated by the vacuum/overpressure unit to blow the sample.

Embodiment 26: A method for producing a nano-suction means which is used in a device for transferring a microscopic, isolated sample, and in particular a membrane-supported micro-dissected specimen, from an object table to an analysis arrangement, with the following method steps: preparing a glass tube; reshaping the glass tube into an approximate L-shape; vapour-plating the glass tube with an electroconductive coating, at least in some sections; attaching a support plate in the form of a disc, this support plate having a hole, with one side on a free end of the glass tube such that the hole in the support plate is more or less flush with the opening in the glass tube; and attaching a terminal mesh on the other side of the support plate such that the terminal mesh covers the opening in the glass tube and the hole in the support plate.

Embodiment 27: The method according to embodiment 26, characterised in that the glass tube is made from borosilicate glass.

Embodiment 28: The method according to embodiment 26 or 27, characterised in that the glass tube is designed with an external diameter of between approx. 1.7 mm and 2.0 mm, an internal diameter of between approx. 0.5 mm and 1.5 mm and an overall length of approx. 50 mm to 70 mm.

Embodiment 29: The method according to at least one of embodiments 26 to 28, characterised in that the glass tube is coated with an electroconductive coating, at least in some sections, and is for example vapour-plated with a gold coating which is approx. 60 nm thick.

Embodiment 30: The method according to at least one of embodiments 26 to 29, characterised in that the support plate is made from an electroconductive material, for example copper.

Embodiment 31: The method according to at least one of embodiments 26 to 30, characterised in that the support plate is attached to the glass tube by means of a UV-hardening adhesive.

Embodiment 32: The method according to at least one of embodiments 26 to 31, characterised in that the L-shaped glass tube has a long section and a short section, the support plate being attached to the end of the short section.

Embodiment 33: The method according to at least one of embodiments 26 to 32, characterised in that the method step of attaching the support plate to the free end of the glass tube includes centring the glass tube exactly over the support plate and lowering it micromechanically until the adhesive-coated edge of the glass tube comes into contact with the support plate.

Embodiment 34: The method according to at least one of embodiments 31 to 33, characterised in that the UV-hardening adhesive is set by means of a UV lamp after joining the glass tube to the support plate.

Embodiment 35: The method according to at least one of embodiments 26 to 34, characterised in that the stage of attaching the terminal mesh to the other side of the support plate includes applying a UV-hardening adhesive, for example in the form of a 0.5 mm wide strip of adhesive, on the other side of the support plate around the hole in the support plate.

Embodiment 36: The method according to embodiment 35, characterised in that the stage of attaching the terminal mesh to the other side of the support plate also includes lowering the glass tube micromechanically together with the attached support plate onto the terminal mesh the supplied adhesive being set with the aid of a UV lamp after joining the support plate and the terminal mesh.

Embodiment 37: The method according to at least one of embodiments 26 to 36, characterised in that the terminal mesh is made from an electroconductive material, and in particular a material with an electroconductive surface.

Embodiment 38: The method according to at least one of embodiments 26 to 37, characterised in that an electroconductive connection is provided between the support plate and the electroconductive coating on the glass tube for earthing purposes, by using an appropriate conductive silver paint or something similar.

LIST OF REFERENCE NUMERALS

1 Suction apparatus
2 Nano-suction means
3 Suction tube
4 Terminal membrane
5 Support plate
6 Terminal mesh
7 Guide connection
8 Hole
9 Opening
10 Coupling tube
11 Connection for vacuum/overpressure unit
12 Carrier apparatus
13 Object table
14 Microscope unit
15 Sample

The invention claimed is:

1. A device for transferring a microscopic, isolated membrane-supported micro-dissected specimen sample, from an object table to an analysis arrangement, with:
a suction apparatus which has a nano-suction apparatus with a suction tube and a terminal membrane and a vacuum/overpressure unit which can be coupled to the nano-suction apparatus for sucking or blowing the sample onto or from the terminal membrane respectively; and
a carrier apparatus for carrying the nano-suction apparatus, which can be moved by an associated positioning unit for positioning the nano-suction apparatus exactly in a sample removal position for sucking the sample onto the terminal membrane and in a sample release position for blowing the sample from the terminal membrane, wherein the terminal membrane has a disc-shaped support plate with a hole in the centre and a terminal mesh, one side of the support plate being secured to the side of the terminal membrane connected to the suction tube in such a way that the hole in the support plate is flush with an opening in the suction tube, and the terminal mesh being secured on the other free side of the support plate in such a way that the terminal mesh overlaps the opening in the suction tube and the hole in the support plate.

2. The device according to claim 1, wherein the nano-suction apparatus can be coupled in an airtight manner to the vacuum/overpressure unit by a coupling tube.

3. The device according to claim 2, wherein the coupling tube has connection devices, plug-in or clip connections, for manual connection of the vacuum/overpressure unit and/or a selected nano-suction apparatus in an airtight fashion on a modular basis in such a way that different nano-suction apparatus at least can easily be coupled manually, in an airtight fashion, to the vacuum/overpressure unit via the coupling tube.

4. The device according to claim 1, wherein the suction tube of the nano-suction apparatus is designed as a borosilicate glass tube.

5. The device according to claim 2, wherein the suction tube is L-shaped and has an end which connects to the coupling tube and an end which connects to the terminal membrane.

6. The device according to claim 1, wherein the suction tube has an external diameter of between approximately 1.7 mm and 2.0 mm, an internal diameter of between approximately 0.5 mm and 1.5 mm and an overall length of approximately 50 mm to 70 mm.

7. The device according to claim 1, wherein the suction tube is coated with an electroconductive coating, at least in some sections, and in the region of the end which is connected to the terminal membrane with a gold coating which is approximately 60 nm thick.

8. The device according to claim 1, wherein the support plate is made from copper.

9. The device according to claim 7, wherein there is an electroconductive connection between the support plate and the electroconductive coating on the suction tube for earthing purposes, by using conductive silver paint.

10. The device according to claim 1, wherein the terminal mesh is made from a material with an electroconductive surface.

11. The device according to claim 1, wherein the terminal mesh has a mesh thickness and a pore size which are adapted to the dimensions and nature of the sample to be transferred, a mesh thickness of approximately 20 μm and pores with a diameter of between approximately 600 nm and 5 μm.

12. The device according to claim 1, wherein the terminal mesh is designed to be biologically inert, antistatic and/or UVC-resistant.

13. The device according to claim 1, wherein the positioning unit is designed for a rotational movement and/or a translational movement of the carrier apparatus by using a micrometer stepper motor.

14. The device according to claim 1, wherein the device also has a laser sensor for measuring the distance between the terminal membrane and the sample to be transferred.

15. The device according to claim 1, wherein the device has a display unit for visual display and monitoring of the transfer of a microscopic, isolated membrane-supported micro-dissected specimen sample.

16. The device according to claim 1, wherein the device has a control unit together with appropriate software which is connected to the carrier apparatus, the positioning unit, the vacuum/overpressure unit, a laser sensor and/or a display unit for data exchange, control and adjustment purposes.

17. The device according to claim 1, wherein the device is designed to be autonomous and can be integrated in a modular fashion in an existing micro-dissection system.

18. A micro-dissection system which includes a device according to claim 1.

19. The micro-dissection system according to claim 18, wherein the micro-dissection system has a microscope unit to which the device can be secured.

20. The micro-dissection system according to claim 19, wherein the device can be secured to the microscope unit in such a way that the carrier apparatus can be moved in a defined manner with respect to a microscope unit reference system.

21. A method for transferring a microscopic, isolated membrane-supported micro-dissected specimen sample, from an object table to an analysis arrangement, with the following method steps:

exact positioning of a nano-suction apparatus, which is designed with a suction tube and a terminal membrane and secured to a carrier apparatus in a sample removal position by moving the carrier apparatus by an associated positioning unit, wherein the terminal membrane has a disc-shaped support plate with a hole in the centre and a terminal mesh, one side of the support plate being secured to the side of the terminal membrane connected to the suction tube in such a way that the hole in the support plate is flush with an opening in the suction tube, and the terminal mesh being secured on the other free side of the support plate in such a way that the terminal mesh overlaps the opening in the suction tube and the hole in the support plate;

suction of the sample onto the terminal membrane by a vacuum/overpressure unit coupled to the nano-suction apparatus;

movement of the carrier apparatus for exact positioning of the nano-suction apparatus in a sample removal position by the associated positioning unit; and blowing the sample from the terminal membrane by the vacuum/overpressure unit.

22. The method according to claim 21, wherein the distance between the terminal membrane and the sample to be transferred is measured continuously by a laser sensor, and is compared with a set value, the height position of the carrier apparatus being adjusted by a control unit until the actual distance value corresponds to the set distance value.

23. The method according to claim 21, wherein an appropriate vacuum is maintained throughout the transfer of a microscopic, isolated membrane-supported micro-dissected specimen sample, from an object table to an analysis arrangement, by the vacuum/overpressure unit.

24. The method according to claim 21, wherein a short pressure pulse is generated by the vacuum/overpressure unit to blow the sample.

* * * * *